US008652542B2

(12) United States Patent
Park et al.

(10) Patent No.: US 8,652,542 B2
(45) Date of Patent: Feb. 18, 2014

(54) COMPOSITION FOR PREVENTING OR TREATING ARTERIOSCLEROSIS

(75) Inventors: Chan-Woong Park, Yongin-si (KR); Dae Bang Seo, Yongin-si (KR); Hee Young Jeon, Yongin-si (KR); Sang Min Lee, Yongin-si (KR); Wan Gi Kim, Suwon-si (KR); Sang Jun Lee, Seongnam-si (KR); Young-Myeong Kim, Chuncheon-si (KR); Chun-Ki Kim, Chuncheon-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 13/131,007

(22) PCT Filed: Nov. 26, 2009

(86) PCT No.: PCT/KR2009/007010
§ 371 (c)(1),
(2), (4) Date: May 24, 2011

(87) PCT Pub. No.: WO2010/062122
PCT Pub. Date: Jun. 3, 2010

(65) Prior Publication Data
US 2011/0268824 A1 Nov. 3, 2011

(30) Foreign Application Priority Data
Nov. 28, 2008 (KR) .................. 10-2008-0119781

(51) Int. Cl.
*A61K 36/258* (2006.01)
(52) U.S. Cl.
USPC .......................................... 424/728; 424/777
(58) Field of Classification Search
None
See application file for complete search history.

(56) References Cited

U.S. PATENT DOCUMENTS

| 6,444,237 | B1 | 9/2002 | Heleen |
| 2002/0012644 | A1 | 1/2002 | Chen |
| 2003/0152544 | A1 | 8/2003 | Chen |
| 2006/0198908 | A1 | 9/2006 | Ko |
| 2008/0267938 | A1 | 10/2008 | Olalde Rangel |

FOREIGN PATENT DOCUMENTS

| CN | 1242374 A | 1/2000 |
| CN | 1440691 | 9/2003 |
| CN | 1628683 A | 6/2005 |
| CN | 1690071 | 11/2005 |
| CN | 1958595 A | 5/2007 |
| JP | 1987-263130 A | 11/1987 |
| JP | 07267977 A | * 10/1995 |
| JP | 2000-212080 | 8/2000 |
| JP | 2002-541872 A | 12/2002 |
| JP | 2003-503012 A | 1/2003 |
| JP | 2003-527304 A | 9/2003 |
| JP | 2005-289913 A | 10/2005 |
| JP | 2008-100999 | 5/2008 |
| KR | 10-2011-0074683 | 8/2001 |
| KR | 10-2007-0032435 A | 3/2007 |
| KR | 10-0780056 B | 4/2007 |
| KR | 10-0823940 B | 4/2008 |
| WO | WO 2005/016362 | 2/2005 |
| WO | WO 2006/115307 | 11/2006 |
| WO | WO 2007/061182 | 5/2007 |

OTHER PUBLICATIONS www.mayoclinic.com/health/arteriosclerosis-atherosclerosis/DS00525/METHOD=print&DSECTION=all—accessed Dec. 2011.*
Dey (Phytomedicine (2003), vol. 10, pp. 600-605).*
Nam et al. (Atherosclerosis (2005), vol. 180, pp. 27-35).*
English translation of Chun (Special Experimental Obstetrics (1984), vol. 2, pp. 32-35).*
Xie et al., "Anti-hyperglycemic effect of the polysaccharides fraction from American ginseng berry extract in *ob/ob* mice," *Phytomedicine* (2004) 11: 182-187.
International Search Report (Form PCT/ISA/210) for corresponding PCT Application No. PCT/KR2009/0007010.
Written Opinion (Form PCT/ISA/237) for corresponding PCT Application No. PCT/KR2009/0007010.
Attele et al., "Ginseng Pharmacology—Multiple constituents and multiple accents," *Biochemical Pharmacology* (1999) 58: 1685-1693.
Chen et al., "Ginsenosides-induced nitric oxide-mediated relaxation of the rabbit corpus cavernosum," *British Journal of Pharmacology* (1995) 115: 15-18.
Choi et al., "Effect of Extraction on Chemical Composition of Red Ginseng Extract," *Korean J. Ginseng Sci.*, vol. 4, No. 1, 1980, pp. 88-95.
Chuang et al., "cGMP mediates corpus cavernosum smooth muscle relaxation with altered cross-bridge function," *Life Sciences* (1998) 63 (3): 185-194.
Crossman, D.C., "More problems with the endothelium," *Q. J. Med.* (1997) 90: 157-160.
Dooley et al., "Development of an in vitro primary screen for skin depigmentation and antimelanoma agents" *Skin Pharmacol* (1994) 7 (4): 188-200. Abstract Only.
Folkman et al., "Angiogenesis," *The Journal of Biological Chemistry* (1992) 267 (16): 10931-10934.

(Continued)

*Primary Examiner* — Susan Hoffman
(74) *Attorney, Agent, or Firm* — Merchant & Gould P.C.

(57) ABSTRACT

A composition according to the present invention is a composition containing extract of *Panax ginseng* C.A. Meyer fruit as an active ingredient for preventing or treating artherosclerosis. The extract is confirmed to effectively suppress lesions or generation of a vascular inflammation factor caused by artherosclerosis. Thus, the composition is suitable for use as an active ingredient of the composition for preventing or treating artherosclerosis.

6 Claims, 7 Drawing Sheets

(56) References Cited

OTHER PUBLICATIONS

Forte et al., "Basal nitric oxide synthesis in essential hypertension," *The Lancet* (1997) 349: 837-842.

Hwang et al., "Quantitative analysis of phenolic compounds in different parts of *Panax ginseng* C.A. Meyer and it's inhibitory effect on melanin biosynthesis," *Korean J. Medicinal Crop Sci.* (2006) 14 (3): 148-152.

Jeong et al., "Therapeutic Angiogenesis," *Journal of Korean Society for Vascular Surgery* (2000) 16 (2): 265-269.

Kang et al., "Ginsenosides of the protopanaxatriol group cause endothelium-dependent relaxation in the rat aorta " *Life Sciences* (1995) 56 (19): 1577-1586.

Korea Ginseng and Tobacco Research Institute, "Chemical Composition of Ginseng," *The Recent Korean Ginseng: Constituents & Effects* (1996) 56-112.

Korea Ginseng and Tobacco Research Institute, "Cultivation of Ginseng," *The Recent Korean Ginseng: Cultivation* (1996) 130-131.

Lee et al., "Antioxidant activities of leaf, steam and root of *Panax ginseng* C. A. Meyer, " *Korean J. Medicinal Crop Sci.* (2004) 12 (3): 237-242.

Leung et al., "Non-genomic effects of ginsenoside-Re in endothelial cells via glucocorticoid receptor," *FEBS Letters* (2007) 581: 2423-2428.

Minghetti et al., "Inductible nitric oxide synthase expression in activated rat microglial cultures is downregulated by exogenous prostaglandin $E_2$ and by cyclooxygenase inhibitors," *GLIA* (1997) 19: 152-160.

Nam et al., "Relationship of saponin and non-saponin for the quality of ginseng," *J. Ginseng Res.* (1998) 22 (4): 274-283.

Office Action for Chinese Patent Application No. 200880018198.9 mailed Jun. 5, 2012.

Office Action for Chinese application No. 2008800181983.9 mailed Jul. 12, 2011.

Park et al., "Biological activities and chemistry of saponins from *Panax ginseng* C.A. Meyer," *Phytochemistry Reviews* (2005) 4: 159-175.

Ryu et al., "Free radical-scavenging activity of Korean Red Ginseng for erectile dysfunction in non-insulin-dependent diabetes mellitus rats " *Urology* (2005) 65 (3): 611-615. ISSN: 0090-4295.

Shao et al., "Antioxidant effects of American ginseng berry extract in cardiomyocytes exposed to acute oxidant stress," *Biochimica et Biophysica* (2004) 1670: 165-171.

Simonsen et al., "Nitric oxide is involved in the inhibitory neurotransmission and endothelium-dependent relaxation of human small penile arteries," *Clinical Science* (1997) 92: 269-275.

Third Party Observation for EP Patent Application No. 08765961.1 and cited art—Kaiyadeva; Kaiyadevanighantau—(Pathyapathyavibodhakah) Edited and translated by P.V. Sharma and Guru Prasad Sharma, Chaukhambha Orientalia, Varanasi, 1$^{st}$ Edition, 1979, p. 642.

Wang et al., "Saponins composition in American ginseng leaf and berry assayed by high-performance liquid chromatography," *Journal of Agricultural and Food Chemistry* (2006) 54: 2261-2266.

Wu et al., "Effects of ginseng fruit saponins (GFS) on coronoary circulation and myocardial oxygen metabolism in dogs with acute myocardial infraction," *Journal of Jilin University (Medicine Edition)* (2006) 32 (3): 428-431.

Xie et al., "Constituents and effects of ginseng leaf," *Oriental Pharmacy and Experimental Medicine* (2004) 4 (1): 1-8.

Xie et al., "The anti-hyperglycemic property of different ginseng partitions," *Oriental Pharmacy and Experimental Medicine* (2005) 5 (1): 1-15.

Yue et al., "Elucidation of the mechanisms underlying the angiogenic effects of ginsenoside $Rg_1$ in vivo and in vitro," *Angiogenesis* (2005) 8: 205-216.

Kang et al, "Ginsenosides of the protopanaxatriol group gause endothelium-dependent relaxation in the RAT aorta," *Life Sciences*, (56)19:1577-86 (1995).

Leung et al, "Non-genomic effects of ginsenoside-Re in endothelial cells via glucocorticoid receptor," *FEBS Letters*, 581:2423-28 (2007).

Seizi, "Hypoxia and NO gene expression," *The way of medicine*, 195:815-16 (2000).

Wang et al, "In vitro anti-cancer activity and structure-activity relationships of natural products isolated from fruits of *Panax ginsing*," *Cancer Chem Pharmacol*, 59:589-601 (2007).

Yue et al, "Elucidation of the mechanisms underlying the angiogenic effects of ginsenoside $Rg_1$ in vivo and in vitro," *Angiogenesis*, 8:205-16 (2005).

Zhao et al., "Effects of IGFS on blood lipid metabolism in experimental hyperlipidemia rats," *Journal of Jilin University (Medicine Edition)*, vol. 31, No. 3, 2005, pp. 407-410 (English Absract).

Jang Soo Chun, "Ginseng fruit chemistry, pharmacology of recent research", *Special Experimental Obstetrics*, vol. 2, 1984, pp. 32-35 (Abstract).

Office Action from Chinese Patent Application No. 200980155347.0 mailed Mar. 1, 2013.

Zhang et al., "Ginsenoside Rg1 Inhibits Tumor Necrosis Factor-α(TNF-α)-Induced Human Arterial Smooth Muscle Cells (HASMCs) Proliferation", *Journal of Cellular Biochemistry*, 98:1471-81 (2006).

Koyama et al., "Inhibitory Effect of Ginsenosides on Migration of Arterial Smooth Muscle Cells", *American Journal of Chinese Medicine*, 20(2):167-73 (1992).

Zhang et al., "Effects of ginsenoside-Rb on blood lipid metabolism and anti-oxidation in hyperlipidemia rats", *China Journal of Chinese Materia Medica*, 29(11):1085-88 (2004).

Japanese Office Action for Japanese Application No. 2011-538548 mailed Jun. 11, 2013.

Jin et al, "Korean red ginseng saponins with low ratios of protopanaxadiol and protopanaxatriol saponin improve scopolamine-induced learning disability and spatial working memory in mice," *Journal of Ethnopharmacology*, (66)2:123-9 (2007).

Choi, "Botanical characteristics, pharmacological effects and medicinal components of Korean *Panax ginseng* C A Meyer," *Acta Pharmacol Sin*, 9:1109-1118 (2008).

Xu et al., "Study on the chemical components of ginseng fruit," *Chinese Traditional and Herbal Drugs* (2007) 38 (5): 667-669.

Attele et al., "Antidiabetic Effects of *Panax ginseng* Berry Extract and the Identification of an Effective Component", *Diabetes*, vol. 51, No. 6, 2002, pp. 1851-1858.

Extended European Search Report for European Application No. 09829329.3 mailed Jan. 28, 2013.

Extended European Search Report for European Application No. 08765961.1 mailed Mar. 8, 2013.

Mehendale et al., "Chronic pretreatment with American ginseng berry and its polyphenolic constituents attenuate oxidant stress in cardiomyocytes", *European Journal of Pharmacology*, vol. 553, 2006, pp. 209-214.

Office Action for Chinese Patent Application No. 201110401114.3 mailed Feb. 5, 2013.

Office Action for Chinese Patent Application No. 201110401145.9 mailed Feb. 27, 2013.

Peng et al., "Antihyperglycemic effects of ginseng and possible mechanisms", *Drugs of the Future*, vol. 33, No. 6, 2008, pp. 507-514.

Yushu et al., "Clinical Study of the Anti-aging Effect of Ginseng Berry Saponin", *Journal of Traditional Chinese Medicine*, No. 10, 1983, pp. 39-41 (English Abstract).

Shao et al., "Antioxidant effects of American ginseng berry extract in cardiomyocytes exposed to acute oxidant stress," *Biochimica et Biophysica Acta*, 1670:165-71 (2004).

Leung et al., "Non-genomic effects of ginsenoside-Re in endothelial cells via glucocorticoid receptor," *FEBS Letters*, 581:2423-28 (2007).

Shi et al., "Investigation of ginsenosides in different parts and ages of *Panax ginseng*", *Food Chemistry*, 102:664-68 (2007).

Office Action from corresponding Korean Patent Application No. 10-2007-0051593 (mailed Sep. 13, 2013).

\* cited by examiner

COMPOSITION FOR PREVENTING OR TREATING ARTERIOSCLEROSIS

This application is a National Stage Application of PCT/KR2009/007010, filed 26 Nov. 2009, which claims benefit of Serial No. 10-2008-0119781, filed 28 Nov. 2008 in the Republic of Korea and which applications are incorporated herein by reference. To the extent appropriate, a claim of priority is made to each of the above disclosed applications.

TECHNICAL FIELD

The present disclosure relates to a composition for preventing or treating arteriosclerosis.

BACKGROUND ART

Ginseng (*Panax ginseng* C.A. Meyer) is a plant belonging to the genus *Panax* in the family Araliaceae. It has been used as a herbal medicine in Korea, China and Japan over 2,000 years. Empirically, it has been used to prevent diseases and prolong lifespan.

Ginsenosides, the physiologically active components of ginseng, are uniformly distributed in the areal and underground parts. Depending on the particular parts, e.g. root, leaves and berry (berries), not only the content but also the composition of the ginsenosides are different.

Recently, vascular dysfunction caused by westernized high-fat diet leads to increased onset of various adult diseases. Cardiovascular diseases including heart attack, arteriosclerosis, stroke, etc. account for 30% of all deaths.

Generally used cardiovascular drugs including angiotensin-converting enzyme (ACE) inhibitors and HMG-CoA reductase inhibitors are mostly expensive synthetic medicine and are problematic in that long-term medication leads to adverse effects.

DISCLOSURE

Technical Problem

The present disclosure is directed to providing a composition for preventing or treating arteriosclerosis capable of effectively suppressing lesions or generation of a vascular inflammation factor caused by arteriosclerosis, which contains an extract of ginseng berry that has not been generally used as an active ingredient.

Technical Solution

In one aspect, the present disclosure provides a composition for preventing or treating arteriosclerosis comprising an extract of ginseng (*Panax ginseng* C.A. Meyer) berry as an active ingredient.

Advantageous Effects

The composition according to the present disclosure, which contains an extract of ginseng (*Panax ginseng* C.A. Meyer) berry, which is different in content and composition from ginseng root, as an active ingredient, is capable of suppressing aortic atheromatous plaques and lesions caused by vascular inflammatory diseases such as arteriosclerosis and significantly reducing generation of the vascular inflammation factor TNF-α and generation of NO caused by activation of iNOS. Thus, it exhibits a superior effect of preventing or treating arteriosclerosis.

MODE FOR INVENTION

Figure 1:
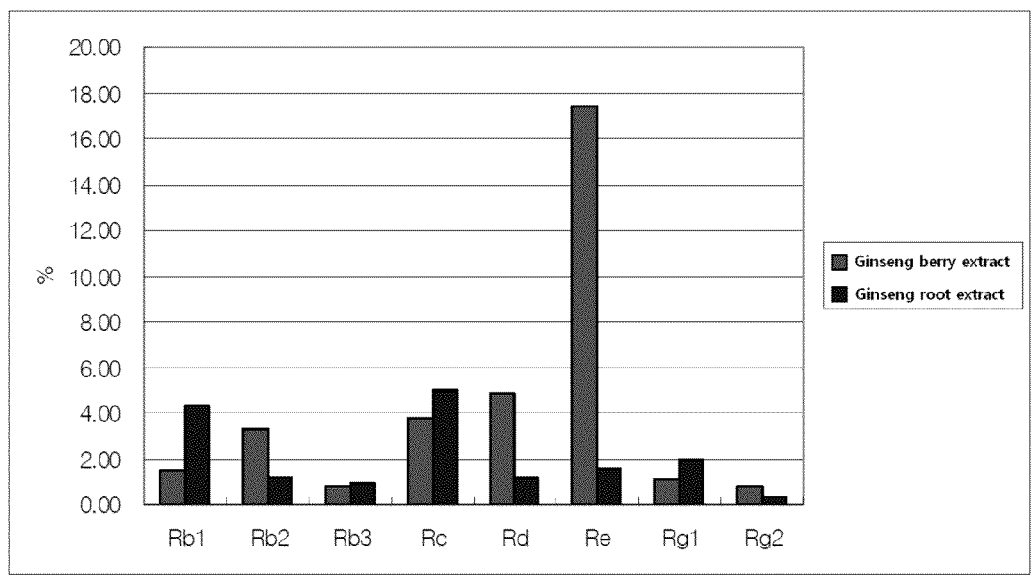
FIG. 1 shows a result graph of analyzing ginsenoside content of ginseng berry and ginseng root extracts by high-performance liquid chromatography (HPLC)

It was confirmed by the inventors of the present disclosure that, as demonstrated through the following examples, treatment with a composition comprising a ginseng berry extract as an active ingredient according to the present disclosure results in reduced fat accumulation on the arterial wall, which increases with the development of arteriosclerosis, as well as significant reduction of lesions caused by arteriosclerosis.

Furthermore, it was confirmed that the composition comprising a ginseng berry extract as an active ingredient is capable of significantly reducing generation of tumor necrosis factor-α (TNF-α) and expression of inducible nitric oxide synthase (iNOS), which are known as the main cause of arteriosclerosis.

In a specific embodiment, the active ingredient may be an extract obtained by drying the pulp and skin of ginseng (*Panax ginseng* C.A. Meyer) berry, with the seed removed, for example, by sun drying or hot air drying and then adding a solvent.

The dried ginseng berry obtained by the pretreatment, i.e. removal of the seed and sun drying or hot air drying of the pulp and skin of the ginseng berry, may be extracted with a solvent, specifically water or ethanol, and concentrated under reduced pressure to obtain the ginseng berry extract.

The ginseng berry extract is different in composition and content from that of the ginseng root. For example, the proportion of protopanaxatriol (PT) ginsenosides to protopanaxadiol (PD) ginsenosides may be 0.5-3.2.

The ginseng berry contains much more ginsenosides than the ginseng root, and is entirely different in composition of the PD ginsenosides Rb1, Rb2, Rc and Rd and PT ginsenosides Re, Rg1 and Rg2 from that of the ginseng root.

Moreover, the ginseng berry extract may include one or more mineral selected from a group consisting of potassium, calcium, iron, phosphorus, magnesium and zinc and/or one or more vitamin selected from a group consisting of vitamin A, vitamin B1, vitamin B2, vitamin B6, vitamin C, vitamin E, vitamin K, vitamin B3 (niacin), vitamin B5 (pantothenic acid) and vitamin B9 (folic acid). These rich minerals and vitamins are also the distinct feature of the ginseng berry as fruit. At this point, the ginseng berry is different from the ginseng root.

Accordingly, the composition comprising the ginseng berry extract as an active ingredient according to the present disclosure is significantly from that comprising the ginseng root extract as an active ingredient in terms of composition.

For example, the extract may be included in an amount of 0.01-100 wt % based on the total weight of the composition. When the content of the extract is 100 wt % based on the total weight of the composition, the composition comprises only the extract as an active ingredient exerting a preventive or therapeutic effect for arteriosclerosis.

Since the composition according to the present disclosure comprises the ginseng berry extract exhibiting anti-arteriosclerotic effect as an active ingredient, it can reduce the formation of lesions caused by arteriosclerosis, which is induced for example by high-fat diet, or suppress the generation of a vascular inflammation factor. The suppression of the vascular inflammation factor may be achieved by the suppression of the generation of TNF-α and inhibition of the expression of iNOS.

For example, the formation of lesions caused by arteriosclerosis may occur as follows. When macrophages that have migrated to the vascular inflammation site engulf oxidized low-density lipoproteins (LDLs), they become foam cells, which produce inflammatory cytokines TNF-α and IL-1β, thus stimulating and promoting proliferation of smooth muscle cells in the tunica media, and migrate toward the tunica intima. As a result, the intima of the artery becomes thicker and protrudes, forming atheromatous plaques (atheroma).

The composition according to the present disclosure may be a food composition or a pharmaceutical composition comprising the ginseng berry extract as an active ingredient, and the food composition may be a functional health food composition.

The pharmaceutical composition according to the present disclosure may comprise an inorganic or organic carrier and may be administered orally in the form of solid, semisolid or liquid, or parenterally via rectal, topical, transdermal, intravenous, intramuscular, intra-abdominal or subcutaneous routes. Specifically, it may be administered orally.

Preparation forms for oral administration may include tablet, pill, granule, soft/hard capsule, powder, fine powder, dust, emulsion, syrup, pellet, drink, etc. And, preparation forms parenteral administration may include injection, drop, ointment, lotion, spray, suspension, emulsion, suppository, etc.

The composition of the present disclosure may be easily prepared according to commonly employed methods. Surfactants, excipients, coloring agents, perfumes, preservatives, stabilizers, buffers, suspensions or other commonly used adjuvants may be used adequately.

The administration dose of the active ingredient will vary depending on the age, sex and body weight of the subject, pathological condition of the particular disease, severity of the disease, administration route, and discretion of the physician. Those skilled in the art may determine the dose based on these factors. A general administration dose may be in the range from 0.001 mg/kg/day to about 2000 mg/kg/day.

The examples and experiments will now be described. The following examples and experiments are for illustrative purposes only and not intended to limit the scope of the present disclosure.

Example 1

Preparation and Analysis of Ginseng (*Panax ginseng* C.A. Meyer) Berry Extract

1. Pretreatment of Ginseng Berry

Live ginseng berry was harvested. After removing the seed, the pulp and skin of the ginseng berry was dried by sun drying or hot air drying to prepare dried ginseng berry.

2. Preparation of Ginseng Berry Extract

Water or ethanol (3 L) was added to dried ginseng berry (1 kg). After extracting at room temperature or under reflux, followed by filtering and concentration at 40-45° C. under reduced pressure, a ginseng berry extract (300 g) was obtained.

3. Compositional Analysis of Ginseng Berry Extract (Comparison of Ginsenosides (Ginseng Saponins) with Ginseng Root)

Ginseng berry extract and ginseng root extract were treated with ether to remove oil-soluble components. Then, crude saponins were extracted with butanol (BuOH), concentrated, and then ginsenoside composition was analyzed by HPLC. The result is given in Table 1 and FIG. 1.

TABLE 1

|  | Ginseng berry extract | Ginseng root extract |
|---|---|---|
| Crude saponins (dry weight) | 33.42% | 16.70% |
| PD/PT ratio | 0.73 | 3.23 |

The ginseng berry extract contained about 2 times more crude saponins than the ginseng root extract. Also, the proportion of protopanaxadiol (PD) ginsenosides (Rb1, Rb2, Rc and Rd) to protopanaxatriol (PT) ginsenosides (Re, Rg1 and Rg2) was distinctly different with 0.73 and 3.23 in the ginseng berry and ginseng root, respectively.

<Analysis of Minerals in Ginseng Berry Extract>

Analysis was performed about mineral and vitamin components of the ginseng (*Panax ginseng* C.A. Meyer) berry extract prepared in Example 1, in order to distinguish a feature of ginseng berry as "fruit" from a feature of ginseng root. The result is given in Table 2.

TABLE 2

| Components | Contents | Components | Contents |
|---|---|---|---|
| Potassium (mg/100 g) | 5865.57 | Magnesium (mg/100 g) | 354.38 |
| Calcium (mg/100 g) | 819.26 | Zinc (mg/100 g) | 178.49 |
| Iron (mg/100 g) | 59.31 | Vitamin A (μg/100 g, RE) | 213.11 |
| Phosphorus (mg/100 g) | 187.17 | Vitamin B1 (mg/100 g) | 12.29 |
| Vitamin B2 (mg/100 g) | 8.45 | Vitamin B6 (mg/100 g) | 10.50 |
| Vitamin C (mg/100 g) | 4.91 | Vitamin E (mg/100 g, α-TE) | 23.61 |
| Vitamin K (μg/100 g) | 231.12 | Niacin (mg/100 g, NE) | 5.76 |
| Pantothenic acid (mg/100 g) | 5.87 | Folic acid (μg/100 g) | 349.97 |

As seen above, the ginseng berry contained more ginseng saponins than the ginseng root. The saponin composition was quite different and the ginseng berry was rich in vitamins and minerals as compared to the ginseng root.

Based on these findings, the effect of preventing or treating arteriosclerosis was investigated. The effect of the ginseng berry extract was compared with that of the red ginseng extract which is widely used as health food.

1. Test Method

Apolipoprotein (ApoE)-deficient mouse was used for the test. Feed and water were given freely for 16 weeks. That is to say, as an animal model commonly employed in the anti-arteriosclerotic test, ApoE-deficient mice were arteriosclerosis-induced for 16 weeks by supplying high-fat diet, and inhibitory effect was examined in the group to which the ginseng berry extract was administered.

1) Preparation of Diet

As a high-fat diet, 20% fat (10% lard, 10% cocoa butter, 0.15% cholesterol and 0.05% cholic acid) was added to the Purina 5001 diet. To the prepared high-fat diet, GB (300 or 500 mg/Kg) or RG (750 mg/Kg) was added. All the feed was sterilized by UV radiation.

2) Test Group Setup

Group 1 (16 mice): high-fat diet (HCD)
Group 2 (16 mice): HCD+GB 300 mg/Kg
Group 3 (16 mice): HCD+GB 500 mg/Kg
Group 4 (16 mice): HCD+RG 750 mg/Kg
Group 5 (8 mice): normal chow diet (NCD)

3) En Face Analysis

The mouse was sacrificed. The heart and the abdominal aorta were cut open and the nearby fat tissue and adventitia were clearly removed. The artery of the basal part of the heart was cut to separate the abdominal aorta from the heart. The abdominal aorta was cut open using operating scissors and tweezers and fixed with pins so that the inside of the blood vessel could be seen. After immobilizing for 16 hours in a 10% neutral buffered formalin solution, the artery was washed with distilled water. The resultant sample was immersed in absolute propylene glycol for 1 minute, stained in an Oil Red O solution for 16 hours, immersed in 85% propylene glycol for 2 minutes, washed with distilled water, and then observed under a dissecting microscope (Leica). The sample image was analyzed using the AxioVision AC imaging software to determine the percentage of lesions of the total area of the aorta.

4) Identification and Area Measurement of Atheromatous Plaques Formed in the Aortic Arch The mouse was sacrificed. The heart and the portion from the ascending aorta to the thoracic aorta were cut and immobilized in a 10% neutral buffered formalin solution. The immobilized heart was trimmed well with a razor, embedded in Optimal Cutting Temperature (OCT) compound, frozen in a deep freezer, and the aortic arch was sliced to 10-μm thickness with a cryostat. For fat staining, thus prepared slides were immersed in distilled water, treated with absolute propylene glycol for 1 minute, stained with an Oil Red O solution for 16 hours, and then treated with 85% propylene glycol for 2 minutes. The slides were washed with distilled water, mounted in aqueous mounting medium, and observed under an optical microscope. From the microscopic image of atheromatous plaques obtained from the optical microscope (Carl Zeiss) equipped with a camera, the area of the plaques was determined using the imaging software.

5) Analysis of Nitric Oxide (NO) in Serum of Arteriosclerotic Mouse Model

The nitrate/nitrite colorimetric assay kit (Cayman Chemical Co., Ann Arbor, Mich.) was used to measure the concentration of NO in serum. According to the provided manual, serum and the standard reagent (40 μL each) were added to a 96-well plate, and an enzyme cofactor mixture (5 μL) was added thereto. After adding a nitrate reductase mixture (5 μL), the resulting mixture was reacted for 3 hours at room temperature. Then, after adding 10% $ZnSO_4$ (50 μL), centrifugation was performed at 1,5000 rpm for 15 minutes. The supernatant (80 μL) was transferred to a 96-well plate and, after adding a Griess reagent 1 solution (40 μL) and a Griess reagent 2 solution (40 μL), reacted for 10 minutes. Absorbance of the reaction product was measured at 550 nm.

6) Analysis of TNF-α in Serum of Arteriosclerotic Mouse Model

Arteriosclerosis results in production of various cytokines through inflammatory response. Among them, TNF-α is the most important cytokine. After the administration of the composition for 16 weeks, blood was taken from the mouse, serum was isolated therefrom, and TNF-α in the serum was identified by ELISA.

2. Test Result

Figure 2A:
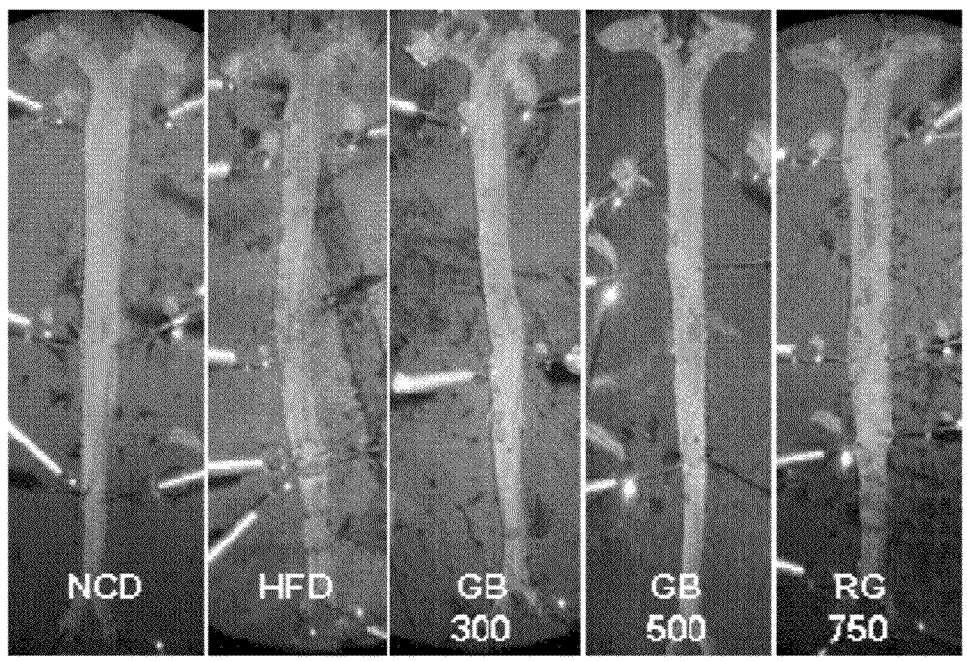
FIG. 2a shows a result picture of measuring formation of atheromatous plaques in the aorta in the groups treated with compositions according to the present disclosure.

1) Identification and Area Measurement of Atheromatous Plaques Formed in the Aorta After supplying a high-fat diet for 16 weeks to ApoE-deficient mice, the aorta was separated and change in atheromatous plaques in the aorta was observed by en face analysis. Increased formation of atheromatous plaques was identified in the high-fat diet group when compared to the normal diet group. The result is shown in FIG. 2a. It was identified that the increase of the atheromatous plaques decreased by the administration of the composition in a concentration-dependent manner.

Figure 2B:
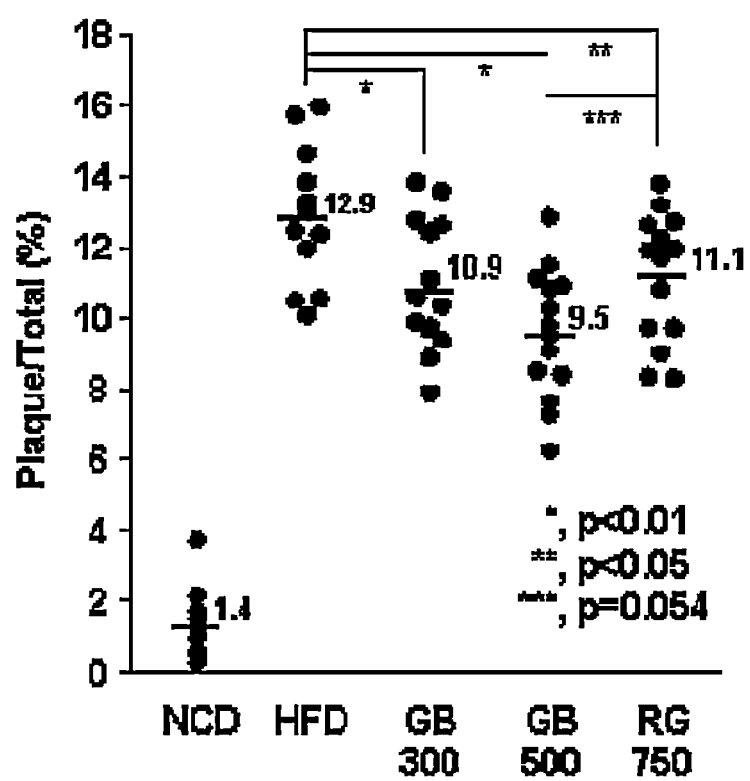
FIG. 2b shows a result graph of measuring formation of atheromatous plaques in the aorta in the groups treated with compositions according to the present disclosure.

The inhibitory effect against the formation of atheromatous plaques was higher in the ginseng berry (GB) extract (500 mg/kg) administration group than the red ginseng (RG) extract (750 mg/kg) administration group. The result is shown in FIG. 2b.

2) Analysis of Lesional Area in the Aortic Arch Through Oil Red O Staining

Figure 3A:
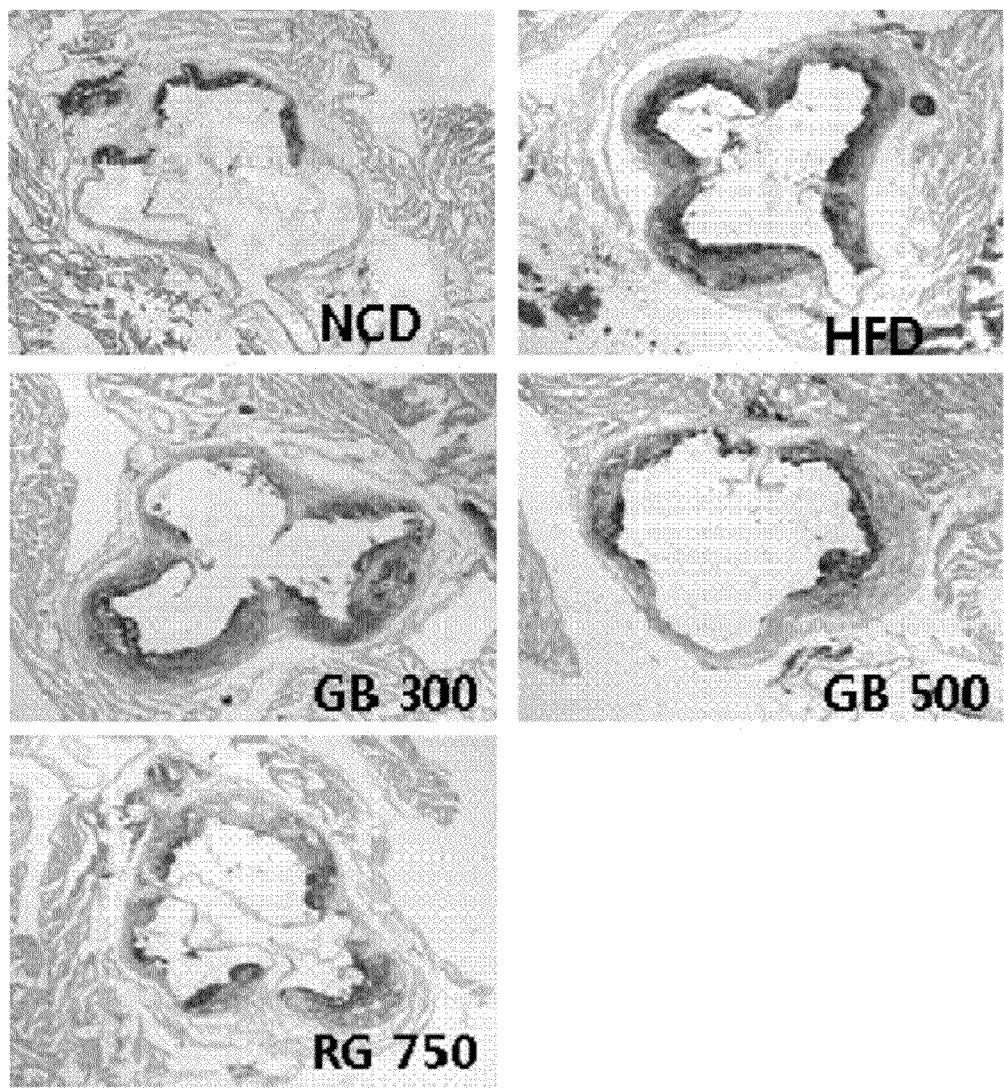
FIG. 3a shows a result picture of measuring lesional area of the aortic arch in the groups treated with compositions according to the present disclosure.
Figure 3B:
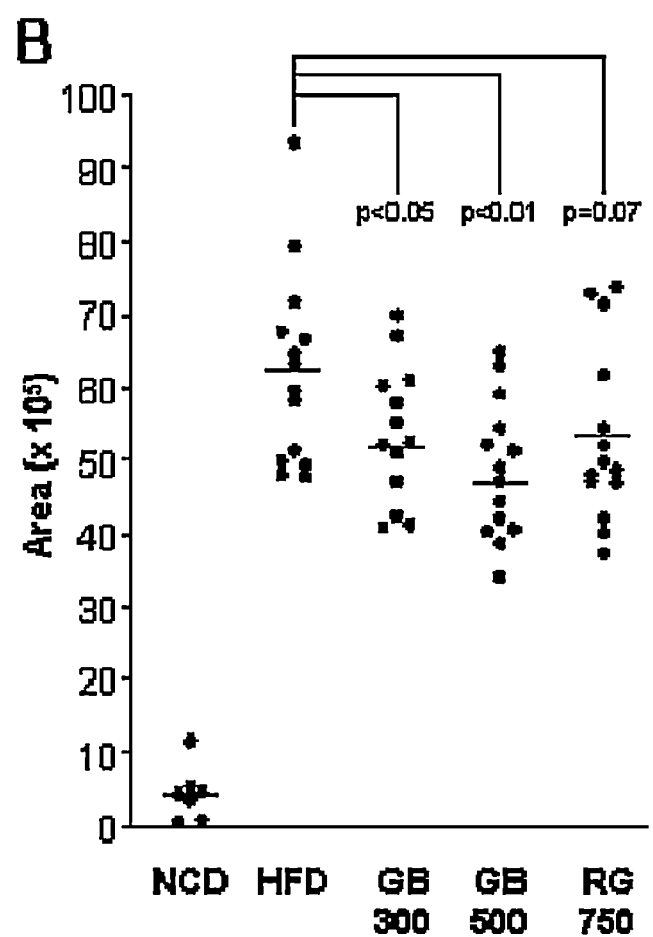
FIG. 3b shows a result graph of measuring lesional area of the aortic arch in the groups treated with compositions according to the present disclosure.

The atheromatous plaques lead to accumulation of fat on the arterial wall. Thus, the inhibitory effect of the administration of the GB composition against the accumulation of fat in the aorta was measured through Oil-red O staining. The high-fat diet group showed remarkably increased atheromatous plaques when compared to the normal control group. The increase of the atheromatous plaques was inhibited by the ginseng berry extract in a concentration-dependent manner. The result is shown in FIG. 3a. The GB (Ginseng Berry extract 500 mg/Kg) administration group showed better effect of reducing lesions in the aortic arch than the RG (Red Ginseng extract 750 mg/Kg) administration group. The result is shown in FIG. 3b.

3) Analysis of Change in Arteriosclerosis-Inducing Factors in Blood

Figure 4A:
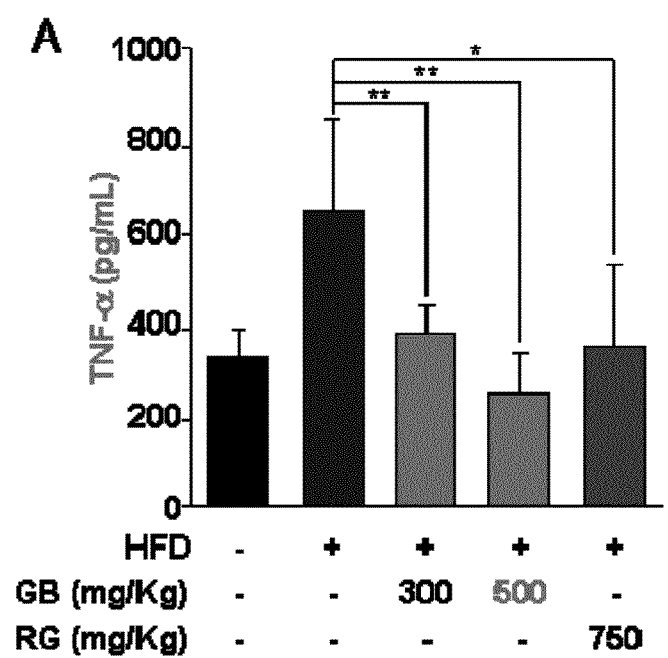
FIG. 4a shows a result graph of analyzing change in generation of an inducing factor of arteriosclerosis, tumor necrosis factor-α (TNF-α), in the groups treated with compositions according to the present disclosure.
Figure 4B:
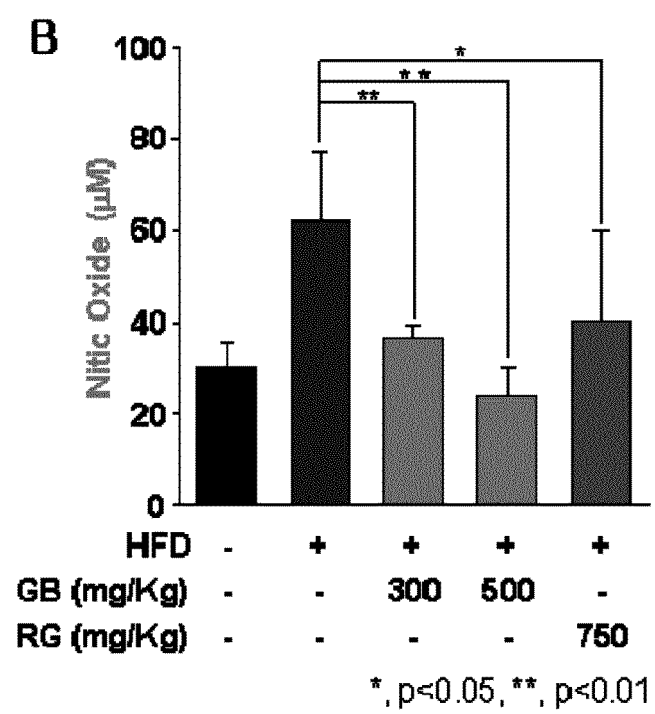
FIG. 4b shows a result graph of analyzing change in generation of nitric oxide (NO) in the groups treated with compositions according to the present disclosure.

The generation of the cytokine TNF-α and the synthesis of nitric oxide due to the expression of iNOS are known as the main cause of the vascular inflammation disease such as arteriosclerosis. Thus, the concentration of TNF-α and nitric oxide in the blood was measured. The high-fat diet group showed increased TNF-α and nitric oxide as compared to the normal diet group. The increase was significantly reduced by the administration of the ginseng berry extract. The result is shown in FIG. 4a and FIG. 4b, respectively. The GB (Ginseng Berry extract 300 mg/Kg) administration group showed better effect of reducing lesions in the aortic arch than the RG (Red Ginseng extract 750 mg/Kg) administration group. The inhibitory effect was the most superior in the GB (Ginseng Berry extract 500 mg/Kg) administration group.

The following preparation examples are for illustrative purposes only and not intended to limit the scope of the present disclosure.

Preparation Example 1

Preparation of Pill

The ginseng berry extract prepared in Example 1 (30 wt %), cornstarch (30 wt %), glycerine (20 wt %) and sorbitol powder (20 wt %) were mixed and prepared into a pill. The final weight of the pill was 3.5 g.

Preparation Example 2

Preparation of Tablet

The ginseng berry extract prepared in Example 1 (30 wt %), lactose (20.5 wt %), dextrin (20 wt %), maltitol powder (20 wt %) and xylitol powder (7 wt %) were mixed, granulated using a fluid-bed dryer, and prepared into a tablet after adding sugar ester (2.5 wt %). The final weight of the tablet was 2 g.

Preparation Example 3

Preparation of Granule

The ginseng berry extract prepared in Example 1 (30 wt %), xylitol (5 wt %) and isomalt (65 wt %) were mixed, formed into a granule using a fluid-bed dryer, and filled in a pouch. The final weight of the granule was 2 g.

Those skilled in the art will appreciate that the conceptions and specific embodiments disclosed in the foregoing description may be readily utilized as a basis for modifying or designing other embodiments for carrying out the same purposes of the present disclosure.

The invention claimed is:

1. A method for treating vascular inflammatory arteriosclerosis of a subject comprising administering to the subject an effective amount of an extract of ginseng (*Panax ginseng* C.A. Meyer) berry that treats arteriosclerosis in the subject, wherein the proportion of protopanaxatriol (PT) ginsenosides to protopanaxadiol (PD) ginsenosides in the extract is 1.4-3.2;
wherein the PT ginsenosides are Re, Rg1, and Rg2; and
wherein the PD ginsenosides are Rb1, Rb2, Rc and Rd.

2. The method according to claim 1, wherein the extract is obtained by drying the pulp and skin of ginseng berry and adding a solvent.

3. The method according to claim 1, wherein the extract is administered in the form of a composition, wherein the composition comprises 0.01-100 wt % of the extract of ginseng berry based on the total weight of the composition.

4. The method according to claim 1, wherein the extract reduces formation of lesions caused by arteriosclerosis.

5. The method according to claim 1, wherein the extract suppresses generation of a vascular inflammation factor.

6. The method according to claim 5, wherein the suppression of the vascular inflammation factor is achieved by the suppression of the generation of tumor necrosis factor-α (TNF-α) and inhibition of the expression of inducible nitric oxide synthase (iNOS).

* * * * *